(12) United States Patent
Kandori et al.

(10) Patent No.: US 8,287,470 B2
(45) Date of Patent: Oct. 16, 2012

(54) SWALLOWING TEST APPARATUS (75) Inventors: Akihiko Kandori, Tokyo (JP); Tsuyoshi Miyashita, Fuchu (JP); Daisuke Suzuki, Kokubunji (JP)

(73) Assignee: Hitachi, Ltd., Tokyo (JP)

( * ) Notice: Subject to any disclaimer, the term of this patent is extended or adjusted under 35 U.S.C. 154(b) by 1114 days.

(21) Appl. No.: 12/155,191

(22) Filed: May 30, 2008

(65) Prior Publication Data
US 2008/0306373 A1  Dec. 11, 2008

(30) Foreign Application Priority Data
Jun. 5, 2007 (JP) .................. 2007-149566

(51) Int. Cl.
A61B 7/00 (2006.01)
A61B 5/103 (2006.01)
A61B 5/117 (2006.01)

(52) U.S. Cl. .......... 600/586; 600/593; 600/595

(58) Field of Classification Search .......... 600/586, 600/593, 595
See application file for complete search history.

(56) References Cited

U.S. PATENT DOCUMENTS
2009/0030346 A1 * 1/2009 Kojima et al. .......... 600/590

FOREIGN PATENT DOCUMENTS
| JP | 9-248282 | 3/1996 |
| JP | 2005-304890 | 4/2004 |
| JP | 2006-95264 | 2/2005 |
| WO | WO 2006013797 A1 * | 2/2006 |

OTHER PUBLICATIONS

Shohei Fujita et al., "Analysis of Beer Drinking Motion Using Swallowing Function Evaluation System SFN-1", IEICE Technical Report, May 2006, pp. 25-28, in Japanese with English abstract.

* cited by examiner

Primary Examiner — Max Hindenburg
Assistant Examiner — Jonathan M Foreman
(74) Attorney, Agent, or Firm — Stites & Harbison, PLLC; Juan Carlos A. Marquez, Esq

(57) ABSTRACT

Disclosed is a swallowing test apparatus including a laryngeal part displacement detection apparatus for detecting a distance of two positions located laterally at a laryngeal part of a subject, a swallowing sound detection apparatus for detecting a swallowing sound of the patient during swallowing, a display, a processing apparatus for displaying a waveform representing the distance of the two positions at the laryngeal part generated based on a signal obtained from the laryngeal part displacement detection apparatus, and a waveform representing the swallowing sound generated based on a signal obtained from the swallowing sound detection apparatus on the display.

7 Claims, 8 Drawing Sheets

FIG.8A
TIME $t_3$

FIG.8A1

FIG.8B
TIME $t_1$

FIG.8B1

FIG.8C
TIME $t_0$

FIG.8C1

FIG.8D
TIME $t_2$

FIG.8D1

FIG.8E
TIME $t_4$

SWALLOWING TEST APPARATUS

CROSS REFERENCE TO RELATED APPLICATIONS

This application claims the foreign priority benefit under 35 U.S.C. §119 of Japanese Patent Application No. 2007-149566 filed on Jun. 5, 2007, the disclosure of which is incorporated herein by reference.

BACKGROUND OF THE INVENTION

1. Field of the Invention

The present invention relates to a swallowing test apparatus which tests the swallowing movement of a biological body (movement that transfers a bolus of food, which is an object to be swallowed, from the oral cavity to the stomach).

2. Description of the Related Art

Dysphagia is caused, for example, by deterioration of physical ability associated with aging or by stroke or cerebral neurological disorder such as Parkinson's disease. A large number of patients are suffered from dysphagia in developed countries including Japan where the aging population is increasing. Patients with dysphagia sometimes misswallow a bolus of food into the bronchial tubes (air passage) or the lung, which may cause pneumonia, leading to high fever. Therefore, when aged people who are short on physical strength are suffered from dysphagia, they are exposed to dangers in which they may lose their life.

As the method for evaluating and determining dysphagia correctly, a VF method (i.e. Videofluoroscopic Examination of Swallowing) is the most common method. In the VF method, an X-ray machine for recording the swallowing movement is used to monitor a bolus of food including contrast media such as barium sulfate that a subject has swallowed. Because the swallowing movement is a series of quick movements, it is common to capture the swallowing movement on video for evaluation. However, the VF method requires extra caution because it has a risk that the subject may misswallow the bolus of food or be suffocated. Moreover, because the VF method uses an X-ray machine, there have been problems of exposure to nuclear radiation, a prolonged test time and costs related to the X-ray machine.

Another method recently introduced is a method for evaluating dysphagia by using a fiberscope. This method is called a Videoendoscopic Examination of Swallowing (VE). The VE method has advantages over the VF method in that a test for dysphagia is carried out easily bringing a fiberscope to a bedside of a patient, and the states of the mucous membranes or tissues of the pharynx and the larynx or saliva retention can be evaluated. However, the VE method also has disadvantages that subjects feel uncomfortable when a fiber is inserted through their nasal cavity, and because a fiberscope apparatus is necessary, a test for dysphagia is still not simple. Thus, the VE method has not been prevailed. Furthermore, the VE method also has a problem that when a bolus of food is transferred into the pharynx, the wall of the pharynx is closed and the space in the pharynx becomes smaller, the view through the fiberscope becomes obscure, and thus the swallowing movement can not be monitored in the time zone in which the organs related to the swallowing movement moves at most in a short time. The time zone is refereed to as "white out", and indicates the limitation of the VE method.

As a method for solving the above problems in the VF method and the VE method, JP Unexamined Patent Publication (Kokai) No. 2005-304890 discloses a method for simply identifying dysphagia correctly without imposing a burden on a patient. In the method disclosed in JP Unexamined Patent Publication (Kokai) No. 2005-304890, electrodes are arranged on a plurality of muscle surfaces concerned with swallowing to record a surface electromyogram, a microphone for recording a swallowing sound is disposed and an acceleration sensor is used for recording the vibration of the throat at the time of the larynx elevation. In the method, patterns of data obtained are learned by neural networks so that dysphagia can be identified.

The method disclosed in JP Unexamined Patent Publication (Kokai) No. 2005-304890, however, has disadvantages that data obtained by the electromyogram, the swallowing sound and the acceleration sensor has to be organized into database and patterns of the data has to be learned by neural networks in order to identify dysphagia, which is time consuming and troublesome. Furthermore, JP Unexamined Patent Publication (Kokai) No. 2005-304890 does not disclose how to differentiate a subject with dysphagia and a healthy subject, and thus it is difficult to use the method in practice. Moreover, in the method, patterns of each kind of data are learned individually without considering relationships of each kind of data, and only a result of a process determining whether or not a subject has dysphagia is output. Thus, the degree of dysphagia can not be represented visually. As described above, JP Unexamined Patent Publication (Kokai) No. 2005-304890 does not disclose techniques of comparing the waveforms of each kind of data, directly determining the degree of dysphagia based on the waveforms of each kind of data, and determining the degree of dysphagia easily. Thus, the method disclosed in the JP Unexamined Patent Publication (Kokai) No. 2005-304890 is poor at visual representation, and it is difficult to determine the degree of dysphagia clinically.

In Non-patent article 1 and JP Unexamined Patent Publication (Kokai) No. 2006-95264, a swallowing motion measuring system is disclosed which uses pressure sensors (for detecting larynx movement), a surface electromyogram and a vibration pickup (for detecting a swallowing sound). Similarly to the method disclosed in JP Unexamined Patent Publication (Kokai) No. 2005-304890, however, the method disclosed in non-patent article 1 evaluates parameters of each kind of data (the value of electromyogram, the time when the output of the pressure sensor is at the maximum, an average cycle and swallowing sound power) independently. Thus, non-patent article 1 also does not disclose techniques of comparing the waveforms of each kind of data, directly determining the degree of dysphagia based on the waveforms of each kind of data, and determining the degree of dysphagia easily. Therefore, the method disclosed in non-patent article 1 is also poor at visual representation, and it is difficult to grasp the degree of dysphagia clinically.

In the method disclosed in non-patent article 1, four pressure sensors are disposed on a sensor box at 8 mm intervals, and the sensor box on which the pressure sensors are disposed is fixed to the neck of a subject by a magic tape (registered trademark) for measuring swallowing movement. However, the four pressure sensors disposed apart from each other are not enough to monitor a series of up and down movements of the thyroid cartilage, and the method only has an accuracy of obtaining the time it takes for a patient to complete the swallowing movement. Furthermore, the method also has a disadvantage that the magic tape has to be wound around the neck of a patent, which is uncomfortable for the patient. Moreover, non-patent article 1 and JP Unexamined Patent Publication (Kokai) No. 2006-95264 does not disclose techniques of comparing the waveforms of each kind of data, directly determining the degree of dysphagia based on the waveforms of each kind of data, and determining the degree of dysphagia easily. Thus, the methods disclosed in non-patent article 1 and JP Unexamined Patent Publication (Kokai) No. 2006-95264 are also poor at visual representation, and it is difficult to grasp the degree of dysphagia clinically.

JP Unexamined Patent Publication (Kokai) No. 2005-304890, JP Unexamined Patent Publication (Kokai) No. 2006-95264 and non-patent article 1 disclose an electromyogram as a basic method for measuring the swallowing movement. However, indifferent electrodes or earth electrodes are necessary in a method using an electromyogram as disclosed in non-patent article 1, which increase the number of electrodes, making it troublesome to manage the electrodes.

Furthermore, in a method using an electromyogram, test results may be different unless electrodes are disposed on accurate positions of the laryngeal part because the laryngeal part includes mainly four kinds of muscles (geniohyoid muscle, thyrohyoideus muscle, sternohyoideus and sternothyroideus) as described in JP Unexamined Patent Publication (Kokai) No. 2005-304890. This problem is inevitable as long as an electromyogram is used. In a method which uses an electromyogram, when a patient himself or an untrained nurse measures swallowing, it is difficult for them to position the electrodes accurately and manage them properly. Moreover, when disposable electrodes are used, there is also a problem that the cost of the disposable electrodes is high.

JP Unexamined Patent Publication (Kokai) No. 9-248282 discloses a method in which two acceleration sensors are attached to a band shaped elastic body, and the two acceleration sensors detect vibration in the throat. An object of this method is to detect an audio signal, pulsation signal or the like. In this method, a swallowing sound is mainly detected, but a detected signal is affected a little by the movement of the laryngeal part and it is difficult to separate these signals, and thus the method is not suitable for evaluating dysphagia.
Non-Patent Article 1: "Shohei FUJITA, Ai MURAYAMA, Toyohiko HAYASHI, Yasuo NAKAMURA, Hidetoshi KOJIMA and Noboru MICHIMI, Analysis of Beer Drinking Motion using Swallowing function evaluation system SFN-1, IEICE Technical Report MBE2006-7(2006-5), p. 25-28, As describe above, because apparatuses used in the VF method and the VE method are large and require a user to be skilled, everybody is not allowed to use the apparatuses to measure swallowing at bed side. The methods disclosed in JP Unexamined Patent Publication (Kokai) No. 2005-304890, JP Unexamined Patent Publication (Kokai) No. 2006-95264 and non-patent article 1 have problems of positioning or managing of electrodes because the methods use an electromyogram, which restricts those who can use these methods. Further, JP Unexamined Patent Publication (Kokai) No. 2005-304890 and non-patent article 1 disclose the methods in which measured data of each kind is analyzed independently, and do not disclose a method for analyzing various kinds of data as a whole or a method for displaying the result of the analysis of the various kinds of data.

SUMMARY OF THE INVENTION

The present invention is made in view of the above problems, and an object thereof is to provide a swallowing test apparatus which enables to test dysphagia easily and display the result of the test.

A first aspect of the present invention provides a swallowing test apparatus including a laryngeal part displacement detection apparatus for detecting a distance between two positions located laterally at a laryngeal part of a subject, a swallowing sound detection apparatus for detecting a swallowing sound of the patient during swallowing, a display and a processing apparatus for displaying a waveform representing the distance of the two positions at the laryngeal part generated based on a signal obtained from the laryngeal part displacement detection apparatus, and a waveform representing the swallowing sound generated based on a signal obtained from the swallowing sound detection apparatus on the display.

Other features and advantages of the present invention will become more apparent from the following detailed descriptions of the invention when taken in conjunction with the accompanying drawings.

BRIEF DESCRIPTION OF THE DRAWINGS

FIGS. 8A1 to 8E1 are schematic views showing the distance between a oscillation coil and a detection coil during swallowing.

DETAILED DESCRIPTION OF THE INVENTION

Swallowing movement is roughly classified into an oral cavity stage, a pharyngeal stage and an esophagus stage. The oral cavity stage refers to a stage where a bolus of food is transferred from an oral cavity to a pharynx. The pharyngeal stage refers to a stage where a swallowing reflex is triggered, and the bolus of food is transferred from the pharynx to an esophagus. The esophagus stage refers to a stage where the bolus of food is transferred from the esophagus to a stomach. The present invention relates to a swallowing test apparatus for detecting dysphagia in the oral cavity stage and the pharyngeal stage. It is to be noted that the swallowing movement of a subject M being tested is initiated by swallowing saliva or a small quantity of water.

Preferred embodiment of the present invention (also referred to as an "embodiment") is described in detail with reference to the accompanying drawings.

Figure 1:
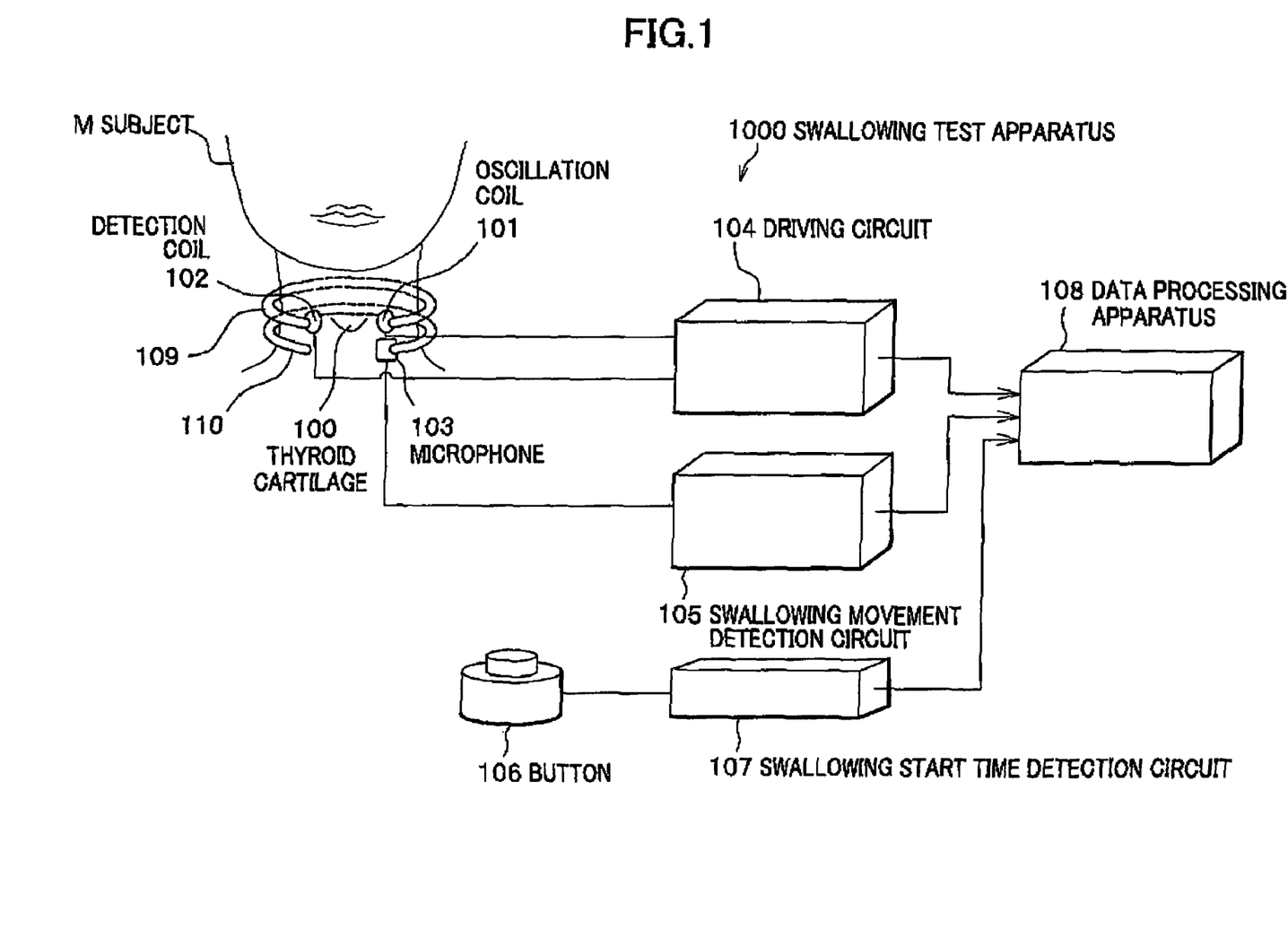
FIG. 1 is an illustration showing an example configuration of a swallowing test apparatus according to an embodiment of the present invention.

FIG. 1 is an illustration showing an example configuration of a swallowing test apparatus according to the embodiment of the present invention.

As shown in FIG. 1, a swallowing test apparatus 1000 includes a oscillation coil 101 (also referred to as a "laryngeal part displacement detection apparatus") and a detection coil 102 (also referred to as the "laryngeal part displacement detection apparatus") held by a flexible holder 109 disposed at the sides of thyroid cartilage 100 (commonly called "Adam's apple") of the subject M. The oscillation coil 101 and the detection coil 102 are connected to a driving circuit 104, and the output voltage output from the driving circuit 104 is input to a data processing apparatus 108. A microphone 103 (also referred to as a "swallowing sound detection apparatus") held by a flexible holder 110 is disposed at the vicinity of the thyroid cartilage. Preferably, the microphone 103 is, for example, a microphone using piezoelectric elements which can focus on the sound of the swallowing movement; however, the microphone 103 may be a condenser microphone. The microphone 103 is connected to the swallowing sound detection circuit 105 and is supplied with an electric power to operate as a microphone. The voltage corresponding to the swallowing sound is output from the swallowing sound detection circuit 105 and then input to the data processing apparatus 108.

The swallowing test apparatus 1000 shown in FIG. 1 further includes a button 106 (also referred to as an "operation apparatus") (may be a switch) for inputting a swallowing start time and a swallowing-movement start time detection circuit 107 connected to the button 106 for detecting a trigger signal representing the start time input by the button 106. The swallowing movement start time detection circuit 107 generates an output signal, for example, by generating and outputting a clock waveform or a digital trigger signal. The output signal output from the swallowing movement start time detection circuit 107 is input to the data processing apparatus 108 and is used as a trigger signal for triggering the data processing apparatus 108 to start acquiring data.

The button 106 may be pushed by a doctor, a nurse or a patient. The data processing apparatus 108 detects a time at which the swallowing sound reaches its peak based on the output voltage output from the swallowing sound detection circuit 105, taking the time when the button 106 is pushed as the swallowing movement start time. The data processing apparatus 108 then detects a time at which the waveform detected by the driving circuit 104 reaches its peak and also detects and analyzes the diphasic complex based on the time at which the swallowing sound reaches its peak. Details of the analyzing process performed by the data processing apparatus 108 is described later.

Figure 3:
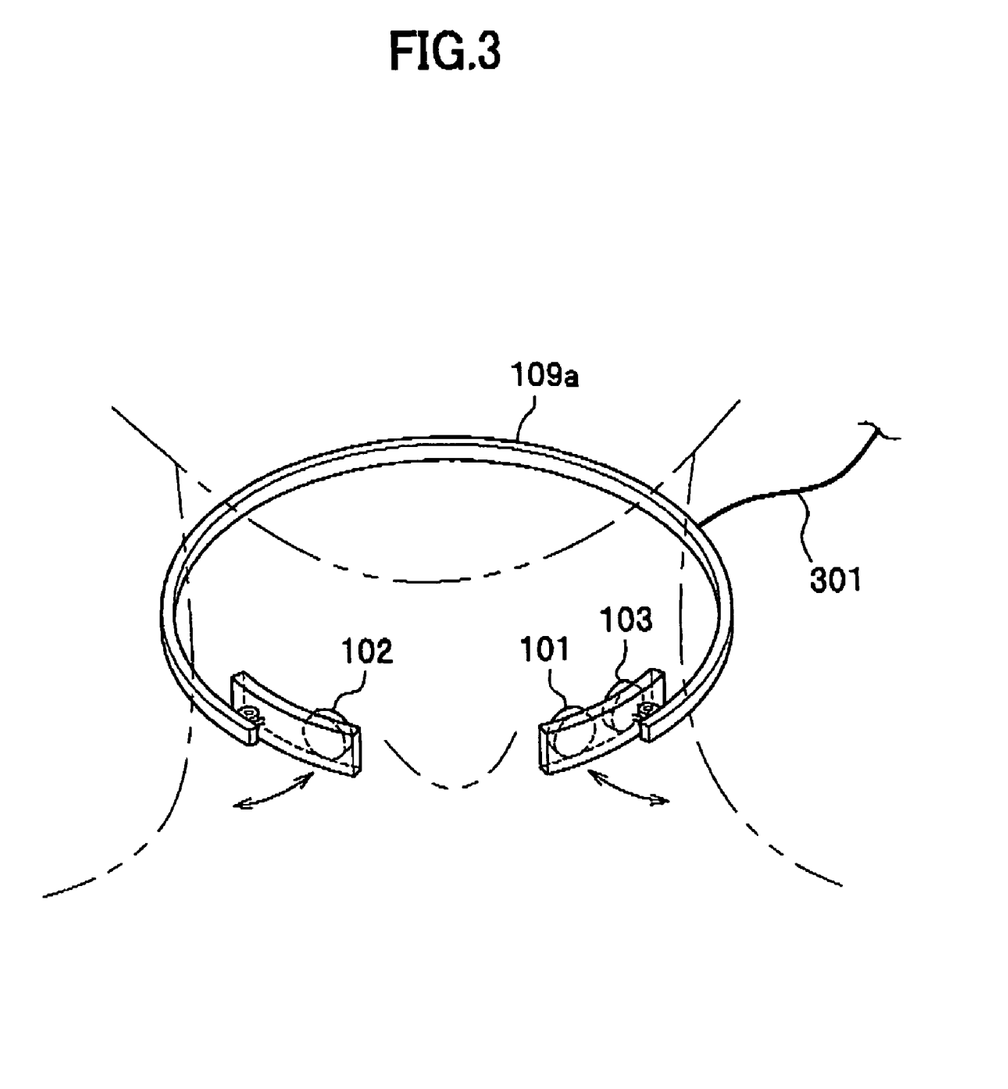
FIG. 3 is an illustration showing an example of a flexible holder.

The oscillation coil 101, the detection coil 102 and the microphone 103 shown in FIG. 1 may be held by only one flexible holder 109a as shown in FIG. 3. The oscillation coil 101 and the detection coil 102 are disposed at a part of the flexible holder 109a which is at the vicinity of the thyroid cartilage as shown in FIG. 3. The microphone 103 is disposed beside the oscillation coil 101 or the detection coil 102 on a side opposite to the thyroid cartilage. The arrangement for disposing the oscillation coil 101 and the detection coil 102 closer allows the oscillation coil 101 and the detection coil 102 to sensitively detect a slight change in magnetic field strength. When the oscillation coil 101 and the detection coil 102 are fixed at the flexible holder 109 or 109a, the oscillation coil 101 and the detection coil 102 are prohibited from being vibrated by the skin of the laryngeal part (around the thyroid cartilage), which makes it possible to sensitively detect a minute change (change of several mm at the maximum) in the distance between the oscillation coil 101 and the detection coil 102 disposed at the laryngeal part. The flexible holders 109, 110, 109a may be made of various types of resins as along as the resins are flexible.

The entire configuration of the swallowing test apparatus 1000 shown in FIG. 1 is described in detail with reference to FIG. 2 (also see FIG. 1 as appropriate). The data processing apparatus 108 includes a processing unit 1081 (also referred to as a "processing apparatus") such as a Central Processing Unit (CPU), a storage unit 1082 such as a Random Access Memory (RAM), Read Only Memory (ROM) and a Hard Disk Drive (HDD), an input unit 1083 such as a keyboard and a display 1084 such as a liquid crystal display.

In the swallowing test apparatus 1000, firstly an alternating voltage generation circuit 206 generates alternating voltage having a predetermined frequency (e.g. 20 kHz). The generated alternating voltage is converted into an alternating current having the predetermined frequency by an alternating current generation amplifier circuit 207. The alternating current then flows into the oscillation coil 101 placed on a biological body.

Magnetic field generated by the oscillation coil 101 induces electromotive force in the detection coil 102 placed on the biological body. The induced electromotive force (which has the same frequency as the predetermined frequency of the alternating voltage generated by the alternating voltage generation circuit) is amplified by a preamplifier circuit 201 (amplifier circuit). The signal which has been amplified is input to a detector circuit 202. The detector circuit 202 demodulates the amplified signal at the predetermined frequency generated by the alternating voltage generation circuit 206 or at double the predetermined frequency. The output voltage of the alternating voltage generation circuit 206 is input to a reference signal input terminal (not shown) of the detector circuit 202 as a reference signal c after the phase of the output voltage is adjusted by a phase adjuster circuit 208.

When demodulation is carried out at double the predetermined frequency, the phase adjuster circuit 208 is not necessary. Simple circuit configuration for performing demodulation at double the predetermined frequency is that the alternating voltage generation circuit 206 is designed to output voltage at double the predetermined frequency, and the frequency of double the predetermined frequency is divided in half by a frequency demultiplier and then is input to the alternating current generation amplifier circuit 207, and the signal of double the predetermined frequency generated by the alternating voltage generation circuit 206 is input to the reference signal input terminal of the detector circuit 202 as the reference signal c. When there is no risk of interference, a full-wave rectifier circuit may be used instead of the detector circuit 202. The above described demodulation is generally referred to as envelope detection, The output of the detector circuit 202 is input to a Low-Pass Filter circuit 203 (LPF) (outputting e.g. a cutoff frequency of 10 Hz) and then amplified by an amplifier circuit 204 to obtain a desired voltage and then is output as an output 205. At last, the output 205 is input into the data processing apparatus 108 and is converted into digital data by an analog-digital conversion board (not shown) incorporated in the data processing apparatus 108. In this configuration, an offset adjust circuit 215 is provided to absorb voltage difference generated in the output 205 by the individual difference of subjects such as the thickness of the neck of the subject. This voltage difference is generated depending on an initial position at which the oscillation coil 101 and the detection coil 102 are disposed (e.g. depending on the thickness of the neck of the subject M). As another method for absorbing the voltage difference, the data processing apparatus 108 may firstly read voltage once and adjust the value of the read voltage.

The voltage difference may be eliminated by a High-Pass filter.

The microphone 103 incorporates an electric current source or is provided with electric power by an external power supply. The output voltage waveform of the microphone 103 has a signal band of several tens of kHz. The full-wave rectifier circuit 210 (also referred to as a "full-wave rectifier") converts a signal obtained from the microphone 103 through a preamplifier circuit 209 into a signal of only one polarity (e.g. only a positive voltage component). The signal is then input into a LPF circuit 211 (using 10 Hz herein) to generate an envelope signal of the swallowing sound signal (envelope detection). The signal band of the swallowing sound may be used without any conversion, however, when the full-wave rectifier circuit 210 and the LPF circuit 211 are employed to generate an envelope signal, the bandwidth of the signal can be made below 10 Hz, which allows the measurement of the signal by using a low sampling frequency of about 100 Hz. This also allows the signal of an output 212 to be within a low frequency band (below 30 Hz), making the sampling frequency used in the swallowing test apparatus 1000 as a whole to be low, whereby the amount of measured data can be reduced.

Figure 2:
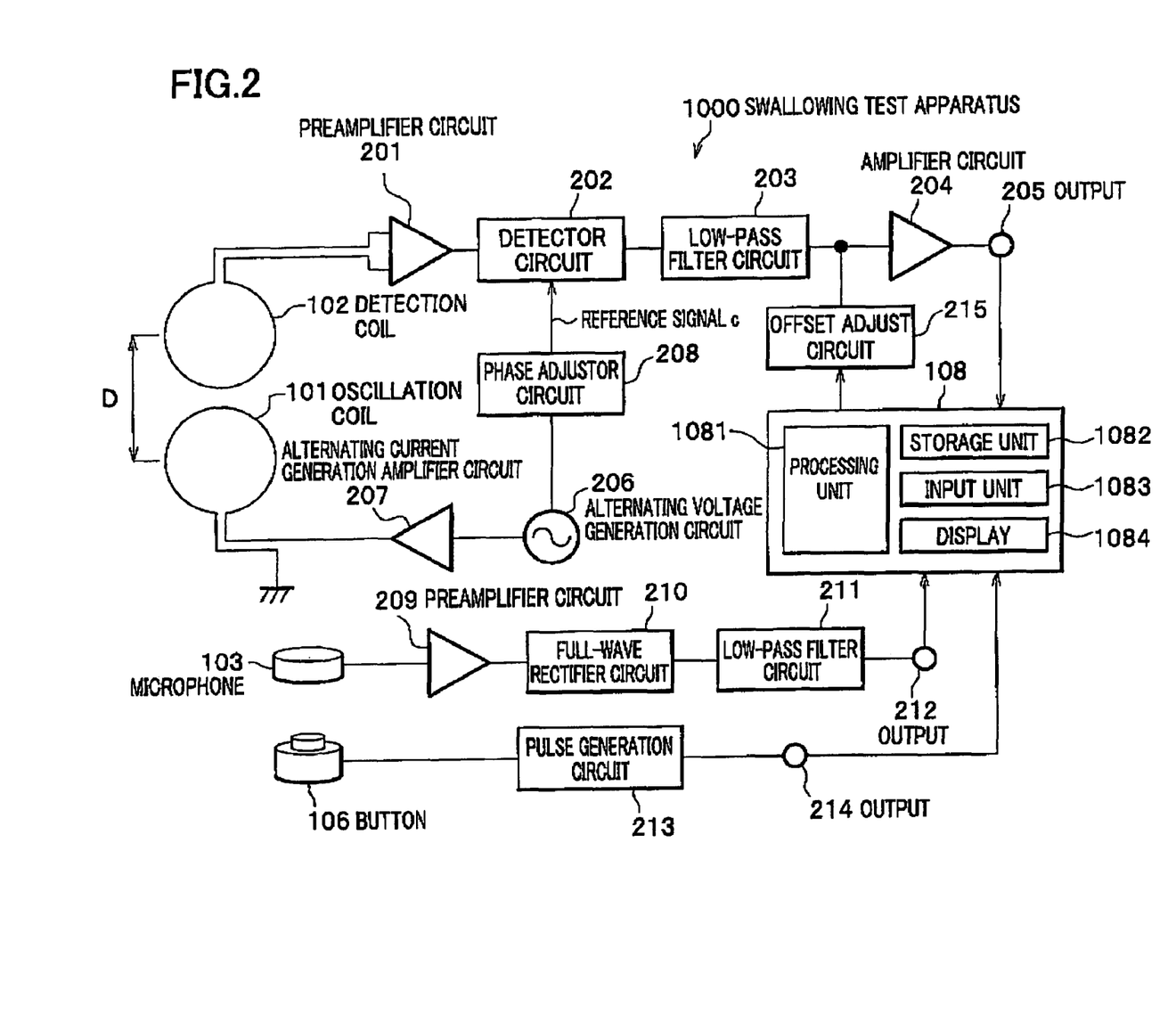
FIG. 2 is an illustration showing the details of overall configuration of the swallowing test apparatus according to the embodiment.

The button 106 shown in FIG. 2 may be various kinds of switches. When the button 106 is pressed, a pulse generator 213 generates and outputs a clock waveform, or a digital trigger signal to generate an output 214. The button 106 and the pulse generator 218 shown in FIG. 2 are only for outputting the start time of the swallowing movement, and thus are not limited to the embodiment and may be realized by various ways such as a configuration using radio waves.

Figure 4A:
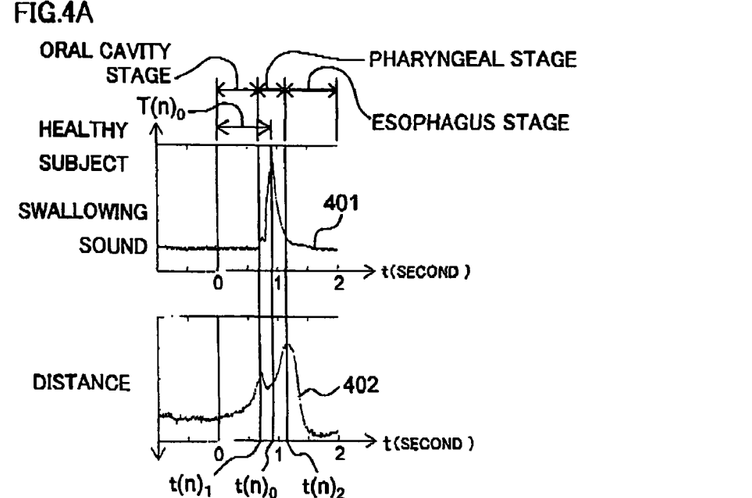
FIG. 4A shows a swallowing sound waveform and a distance waveform of a healthy subject.
Figure 4B:
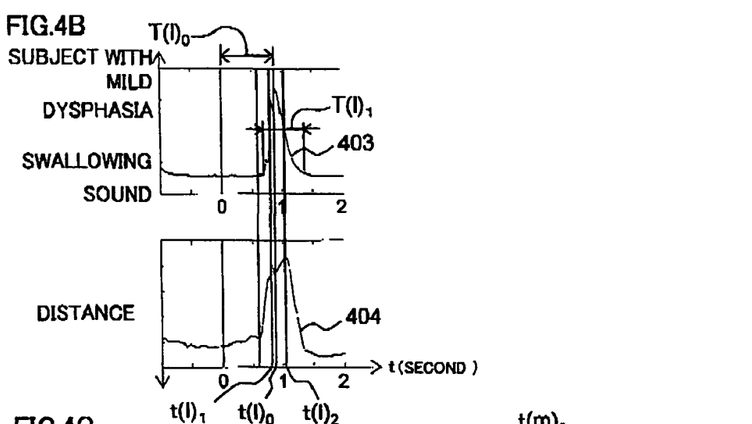
FIG. 4B shows a swallowing sound waveform and a distance waveform of a subject with mild dysphagia.
Figure 4C:
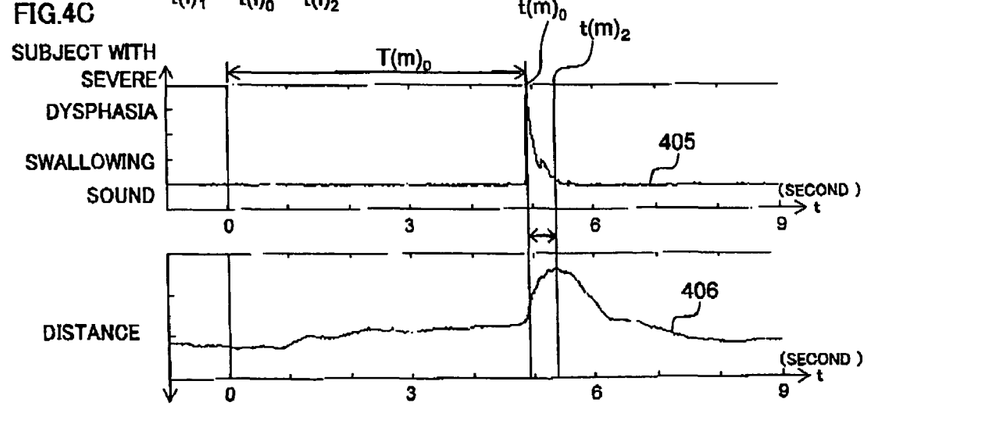
FIG. 4C shows a swallowing sound waveform and a distance waveform of a subject with severe dysphagia.

FIG. 4 shows an example data of a healthy subject and subjects with dysphagia which is measured by the swallowing test apparatus 1000 shown in FIG. 1 and FIG. 2 (refer to other figures as appropriate). The example data shown in FIGS. 4A to 4C is displayed on the display 1084 of the data processing apparatus 108.

FIG. 4A shows a swallowing sound waveform 401 and a distance waveform (waveform of voltage between the coils) 402 of a healthy subject. FIG. 4B shows a swallowing sound waveform 403 and a distance waveform (waveform of voltage between the coils) 404 of a subject with mild dysphagia. FIG. 4C shows a swallowing sound waveform 405 and a distance waveform (waveform of voltage between the coils) 406 of a subject with severe dysphagia. It is to be noted that the distance between the oscillation coil 101 and the detection coil 102 becomes longer as the distance waveforms 402, 404 and 406 go down.

In FIG. 4A, a time t(n) 0 represents the peak (the maximum value) time of the swallowing sound. A time t(n) 1 represents the minimum peak (the minimum value) time of the distance before the peak time t(n) 0 of the swallowing sound. A time t(n) 2 represents the minimum peak (the minimum value) time of the distance after the peak time t(n) 0 of the swallowing sound. T(n) 0 represents a time interval from the swallowing movement start time (indicated as 0, which is the time the button 106 is operated) to the peak time t(n) 0 of the swallowing sound.

As shown in FIG. 4A, a characteristic of the healthy subject is that the distance waveform 402 includes the two peaks. The time intervals of the oral cavity stage, pharyngeal stage and the esophagus stage in the swallowing movement are as shown in FIG. 4A.

In FIG. 4B, the values of a time t(l)0, t(l)1 and t(l)2 and a time interval T(l)0 are similar to the values of the time t(n)0, t(n)1 and t(n)2 and the time interval T(n)0 shown in FIG. 4A, however, the shape of the distance waveform 404 is different from that of the distance waveform 402 (details will be described later).

In FIG. 4C, the waveform between a time t(m)0 and a time t(m)2 is similar to that between the time t(n)0 and the time t(n)2 shown in FIG. 4A, however, the distance waveform 406 significantly differs from the distance waveform 402 in that the distance waveform 406 does not have a peak before the peak time t(m)0 of the swallowing sound (details will be described later).

More specifically, the distance waveform of the healthy subject is U-shape having two peaks at the sides of the peak time of the swallowing sound (a cause of generation of the U-shape will be described with reference to FIG. 8).

On the other hand, the distance waveform of the subject with dysphagia is likely to have only one peak. Moreover, the distance waveform of the subject with dysphagia does not show the prominent maximum value around the peak time of the swallowing sound. In the swallowing sound waveform 405 and the distance waveform 406 of the subject with severe dysphagia, the time interval T(m)0 from the swallowing movement start time (0) when the button 106 is operated to the peak time t(m)0 of the swallowing sound is long, which indicates the delay of the swallowing movement of the bolus of food. Furthermore, in the distance waveform 406, the time interval between the peak time t(m)0 of the swallowing sound and the time t(m)2 is also long.

As described above, by displaying the swallowing sound waveform and the distance waveform at the same time, a user of the 1000 can see the degree of time delay of the swallowing movement and whether or not the distance waveform has only one peak. This allows the user to see the movement of the epiglottis (refer to FIG. 8), whereby the degree of dysphagia can be visually grasped. Furthermore, the degree of dysphagia can be quantitatively grasped based on the degree of time delay of the movement of the epiglottis which is calculated based on the peak time of the swallowing sound.

Figure 5:
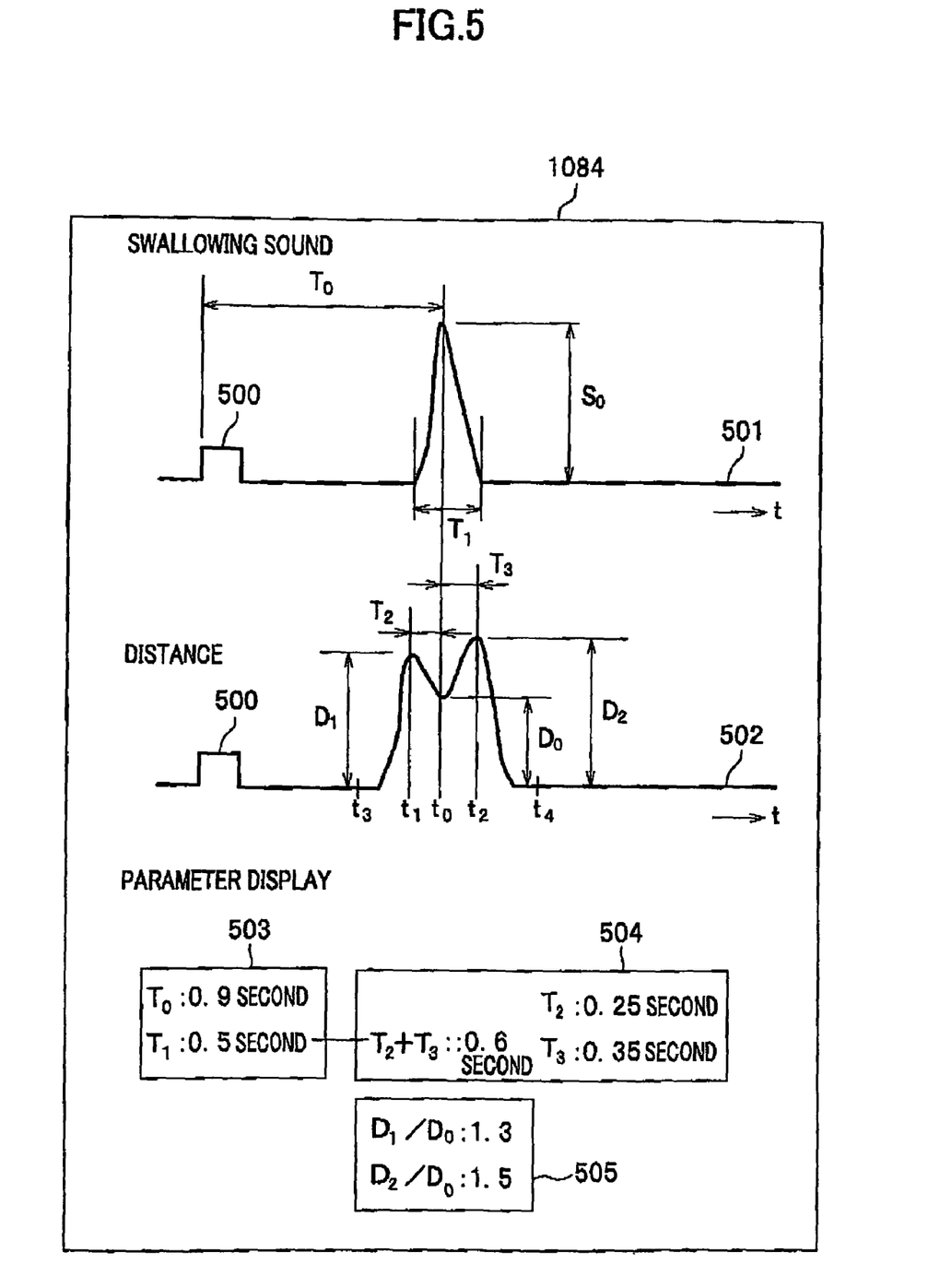
FIG. 5 is an illustration for explaining a method for analyzing the swallowing sound waveform and the distance waveform in the swallowing test apparatus according to the embodiment.

FIG. 5 is an illustration explaining a waveform analysis (refer to other figures as appropriate). The screen for the waveform analysis is displayed on the display 1084 of the data processing apparatus 108, and the processing unit 1081 performs processing or calculation for the waveform analysis.

In FIG. 5, a swallowing movement start clock 500 generated when the button 106 is operated is displayed for both of the swallowing sound waveform 501 and the distance waveform (waveform of voltage between the coils) 502 to allow a user to easily see the swallowing movement start time. The time interval between the swallowing movement start clock 500 and the peak time of the swallowing sound waveform 501 is represented as T0, and the peak time of the swallowing sound is represented as t0. The strength of the swallowing sound at the peak time t0 is S0. Based on the peak time t0 of the swallowing sound as a reference, a time interval T1 from the start of the swallowing sound to the end of the swallowing sound is detected. To automatically detect the time interval T1, a method may be employed which detects a time at which the strength of the swallowing sound is half or the specified faction (e.g. a tithe) of the strength S0 of the swallowing sound.

As for the distance waveform 502, a voltage strength D0 at the time t0, a voltage strength D1 at a peak time t1 of the distance waveform 502 before the time t0 and a voltage strength D2 at a peak time t2 of the distance waveform 502 after the time t0 are automatically detected. Furthermore, a time interval T2 between the time t1 and the time t0 and a time interval T3 between the time t0 and the time t2 are automatically detected.

A time parameter display part 503 related to the swallowing sound waveform, a time parameter display part 504 related to the distance waveform and a distance ratio parameter display part 505 related to the distance waveform are also displayed together with the swallowing sound waveform 501 and the distance waveform 502 on the same screen to allow the user to visually identify dysphagia easily. The user can see the time it takes for a bolus of food to be transferred to an esophagus from an oral cavity by referring to the time T0 and T1 shown in the time parameter display part 603 related to the swallowing sound waveform.

The user is allowed to see whether or not the distance waveform has only one peak or the movement of the epiglottis is delayed by refereeing to T2 or T3 related to the distance waveform shown in the time parameter display part 504. The user is also allowed to determine whether or not the time interval in which a bolus of food is transferred from the pharynx to the esophagus is substantially the same as the time interval in which the epiglottis is opened and then closed by comparing the sum of the values of T2 and T3 with the value of T1. In the example of a subject with mild dysphagia shown in FIG. 4B, the value of T1 is greater than the sum of the values of T2 and T3.

By displaying the time parameter display part 503 related to the swallowing sound waveform, the time parameter display part 504 related to the distance waveform and the distance ratio parameter display part 505 related to the distance waveform together with the swallowing sound waveform 501 and the distance waveform 502 on the same screen as described above, the user is allowed to visually and quantitatively grasp the degree of dysphagia easily. Various types of parameters such as the time parameters and the voltage ratios may be displayed on the swallowing sound waveform and the distance waveform indicated by additional lines.

A processing flow of detecting the time parameters (t0, t1, t2, T1, T2 and T3), the voltage strengths (D0, D1 and D2) and the maximum amplitude value of the swallowing sound (S0) shown in FIG. 5 is described with reference to FIG. 6 (refer to other figures as appropriate). A processing unit 1081 of the data processing apparatus 108 performs the processing flow. Times t3 and t4 are described later.

The processing unit 1081 displays the swallowing sound waveform and the distance waveform (waveform of voltage between the coils) on the display 1084 (step S601). The processing unit 1081 firstly detects the peak time t0 at which the amplitude of the swallowing sound is the maximum and the maximum amplitude value (S0) at the peak time t0 (step S602) from the swallowing sound waveform displayed on the display 1084. Next, the processing unit 1081 detects the time interval T1 for which the swallowing sound keeps emitting by detecting the time at which the amplitude of the swallowing sound is half or a fraction (e.g. tithe) of the value of S0 or the time at which the amplitude of the swallowing sound exceeds a specified threshold value (step S603).

The processing unit 1081 then detects parameters related to a diphasic complex distance waveform symmetry with respect to the time (t0), such as the time interval T2, the time interval T3, the voltage strength D1 at the time t1 and the voltage strength D2 at the time t2 (step S604). To be more specific, the processing unit 1081 detects the time t1 at which the amplitude of the distance waveform is the maximum before the peak time t0 of the swallowing sound, and further detects the voltage strength D1 of the distance waveform at the time t1. The processing unit 1081 also detects the time t2 at which the amplitude of the distance waveform is the maximum after the peak time t0 of the swallowing sound, and further detects the voltage strength D2 of the distance waveform at the time t1.

The processing unit 1081 then calculates the ratios of D1 to D0, D2 to D0 or the like to clarify the relationships of the voltage strengths D0, D1 and D2 (step S605).

By calculating these ratios, it is possible to absorb the individual differences of the subjects M and the difference of the positions on which the oscillation coil 101 and the detection coil 102 are disposed. Moreover, the voltage between the oscillation coil 101 and the detection coil 102 represents just a distance change of several mm; hence the precise value of the distance change of several mm can be obtained without converting the voltage between the oscillation coil 101 and the detection coil 102 into a precise value representing distance.

By performing the processing described above, the processing unit 1081 can display each parameter together with the swallowing sound waveform and the distance waveform (step S606) (refer to FIG. 5).

After step 606, the processing unit 1081 performs processes for determining dysphagia, and displays results of the processes on the display 1084 (step 607). Step 607 is described in detail with reference to FIG. 7 (refer to other figures as appropriate).

Figure 6:
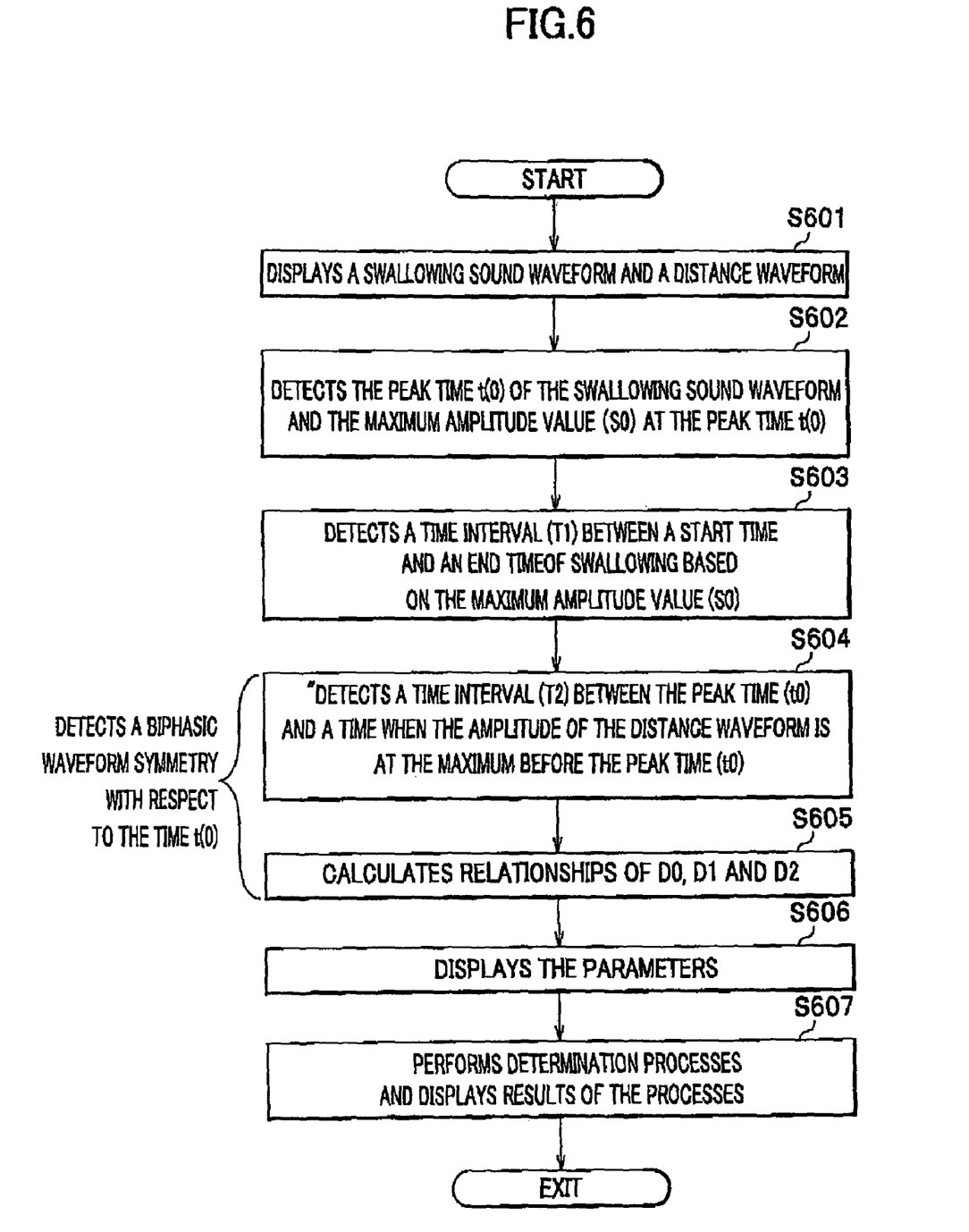
FIG. 6 is a flowchart showing a process for detecting time parameters, voltage strengths and the maximum amplitude of the swallowing sound.
Figure 7:
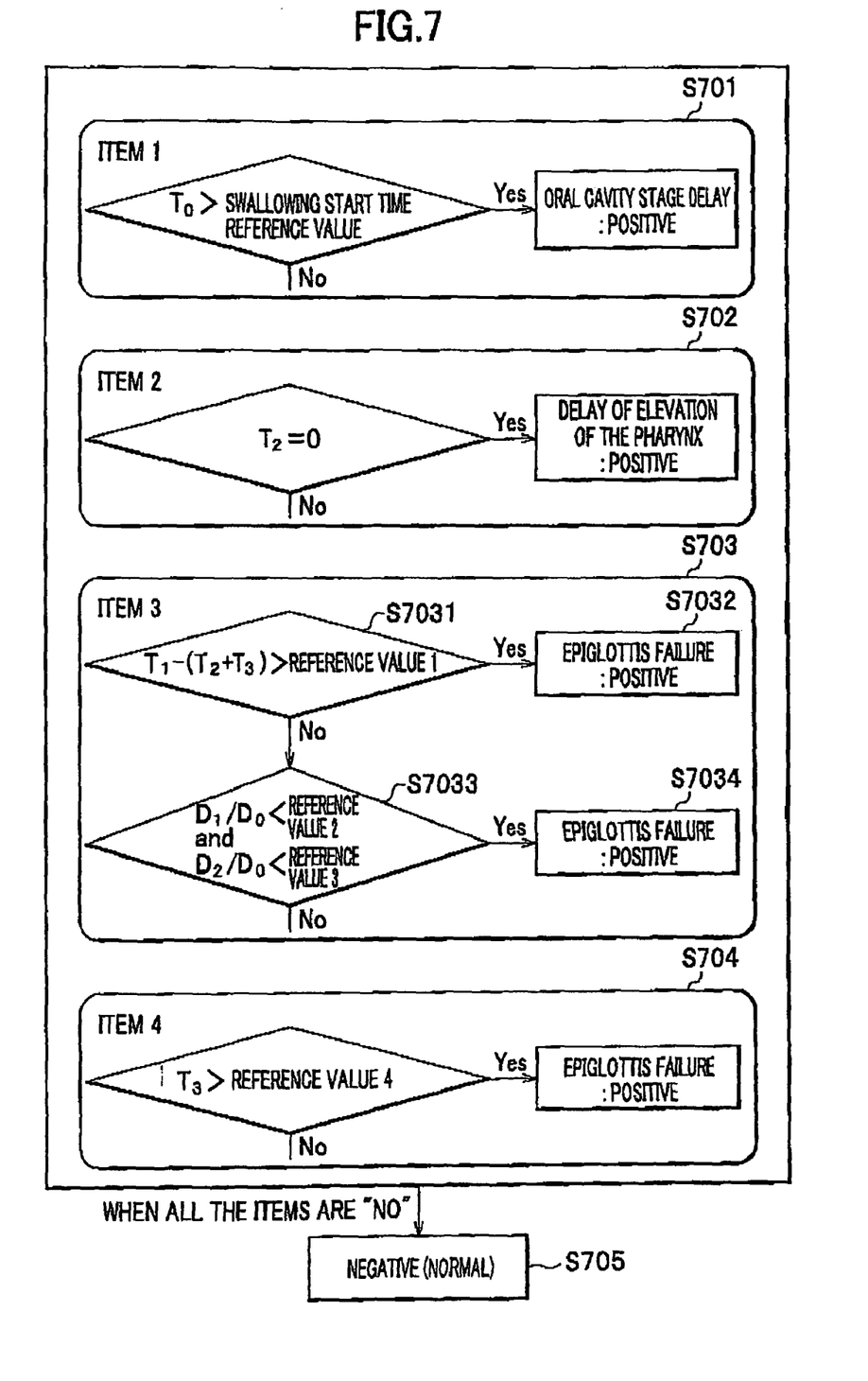
FIG. 7 is an illustration for explaining example processes for determining dysphagia and display of the results of the processes.

FIG. 7 is an illustration for explaining processes for determining dysphagia and the display of the results of the processes (corresponding to step S607 in FIG. 6). The processing unit 1081 of the data processing apparatus 108 performs the processes. The processes for determining dysphagia and the display of the results of the processes are not limited to the way shown in FIG. 7, however, the most appropriate process for determining dysphagia and the most appropriate display of the result of the process can be realized by adding items which are clinically necessary or deleting items as appropriate. In the determining processes shown in FIG. 7 (and FIGS. 5 and 6), all the processes for determining dysphagia are performed by calculating the amount of characteristic of the distance waveform based on a reference time (the time t0 in this embodiment) which is derived from the swallowing sound waveform.

The processes shown in FIG. 7 determine whether or not the subject M is dysphagia based on four items. The process at step S701 compares the time interval T0 between the time 0 at which the swallowing movement starts (the button 106 is operated) and the peak time of the swallowing sound with a swallowing start time reference value (e.g. one second). When the time interval T0 is greater than the swallowing start time reference value (Yes at step 701), the processing unit 1081 determines that the oral cavity stage (swallowing time) is delayed and displays "oral cavity stage delay: positive".

The process at step 702 determines whether or not the time interval T2 is 0. When the time interval T2 is 0 (Yes at step 702), which means that the distance waveform has no peak before the time t0, the processing unit 1081 determines that elevation of the pharynx is delayed and displays "delay of elevation of the pharynx: positive".

The process at step 703 includes two steps for determining epiglottis failure.

At a first step, the processing unit 1081 determines whether or not the value obtained by subtracting the sum of the time intervals T2 and T3 from the time interval T1 between the start of the swallowing sound and the end of the swallowing sound is greater than a reference value 1 (e.g. 0.1 second) (step 7031). When the value is greater than the reference value 1 (Yes at step 7031), which means the subject M has a epiglottis failure where the movement of the epiglottis is finished before a bolus of food is passed to the esophagus, the processing unit 1081 displays "epiglottis failure: positive" (step 7032). When the value is less than the reference value 1 (No at step 7031), the process continues to determine whether or not the ratio D1 to D0 is less than a reference value 2 (e.g. 1.1) and the ratio D2 to D0 is less than a reference value 3 (e.g. 1.2) (step 7033). When the ratio D1 to D0 is less than the reference value 2 and the ratio D2 to D0 is less than the reference value 3 (Yes at step 7033), which means that the subject M has epiglottis failure where the distance waveform is not a biphasic waveform, the processing unit 1081 displays "epiglottis failure: positive" (step 7034).

The process at step 704 compares the time interval T3 with a reference value 4 (e.g. 0.5 second). When the time interval T3 is longer than the reference value 4 (yes), which means the subject M has epiglottis failure, the processing unit 1081 displays "epiglottis failure: positive" (step 704).

When all the processes of steps 701 to 704 determines "No", all the items are displayed as "negative" (step 705).

The processes for determining dysphagia are performed and the results of the processes are displayed as described above.

Figure 8A:
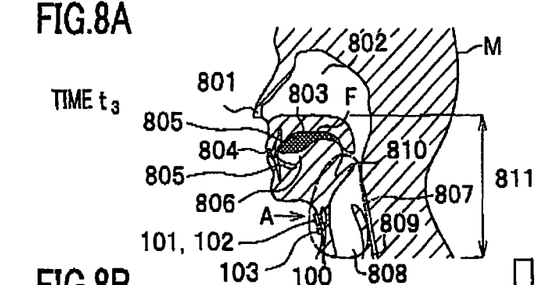
FIGS. 8A to 8E are illustrations showing states of inside of the body of a subject M during swallowing.
Figure 8A:
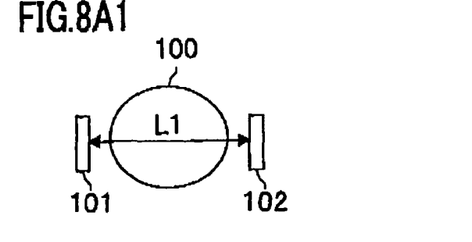
Figure 8B:
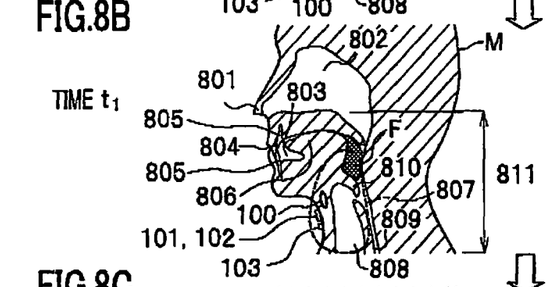
Figure 8B:
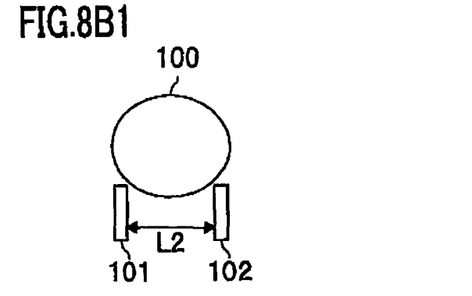

The movements of the laryngeal part and the pharynx at the time of the swallowing movement are described with reference to FIG. 8 (see other figures as appropriate). States inside of the body of the subject M during the swallowing movement is firstly described with reference to FIGS. 8A to 8E. Then, the distance between the oscillation coil 101 and the detection coil 102 in each figure is explained referring to FIGS. 8A1 to 8E1. The times at which the states of the subject M are described in FIGS. 8A to 8E corresponds to the times t3, t1, t0, t2 and t4 shown in FIG. 5 respectively. The times t3 and t4 respectively represent the times immediately before and after the distance waveform 502 (refer to FIG. 5) changes. FIG. 8A1 is a schematic view of the subject M seen in the direction indicated by an arrow A shown in FIG. 8A. FIGS. 8B1 to 8E1 are also schematic views of the subject M, similarly to FIG. 8A1.

A nasal cavity 802 is located inside of the nose 801 of the subject M, teeth 805 and an oral cavity 803 are located inside of a mouth 804 as shown in FIG. 8A. At the time t3, a bolus of food F is on a tongue 806. Located at the lower part of a pharynx 811 is a laryngeal part 807. An epiglottis 810 in the laryngeal part 807 extends upward, the nasal cavity 802 is connected to a windpipe 808, and an esophagus 809 is closed. The oscillation coil 101 and the detection coil 102 are disposed on the sides of the thyroid cartilage 100, and the microphone 103 is also disposed just below the oscillation coil 101 and the detection coil 102.

At the time t1, the bolus of food F is transferred to the laryngeal part 807, a thyroid cartilage 100 moves up, and the epiglottis 810 moves down so as to block the passageway from the nasal cavity 802 to the windpipe 808 as shown in FIG. 8B. When the movement of the tongue 806 is not normal, the bolus of food F is not transferred from the oral cavity 803 to the laryngeal part 807 normally (takes time).

Figure 8C:
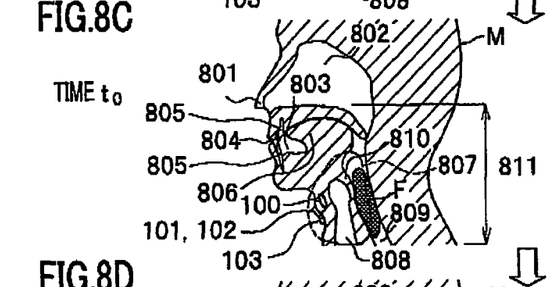
Figure 8C:
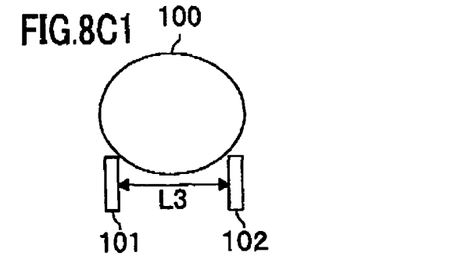

At the time t0, the epiglottis 810 blocks the passageway from the nasal cavity 802 to the windpipe 808, and the bolus of food F is passed beside the epiglottis 810 as shown in FIG. 8C. At this time, the thyroid cartilage 100 moves forward (in the direction subject M faces). When the movement of the epiglottis 810 is not normal, the passage way from the nasal cavity 802 to the windpipe 808 is not completely blocked, and thus a part of the bolus of food F is aspirated into the windpipe 808.

At the time t2, the bolus of food F has finished passing beside the epiglottis 810 and the epiglottis 810 starts moving up to return to the original position, and the thyroid cartilage 100 also moves backward to return to the position shown in FIG. 8B, as shown in FIG. 8D.

At the time t4, the bolus of food F has finished passing beside the laryngeal part 807, and the epiglottis 810 and the thyroid cartilage 100 return to their original positions shown in FIG. 8A respectively, as shown in FIG. 8E.

In the above described swallowing movement, the distance between the oscillation coil 101 and the detection coil 102 changes as shown by L1 to L5 in FIGS. 8A1 to 8E1. The reasons why the distance L3 in FIG. 8C is longer than the distance L2 are considered to be that the laryngeal part is raised by the forward directional movement of the thyroid cartilage 100, which is caused by the closing of the epiglottis 810, a pair of the arytenoid cartilages (not shown) inside of the thyroid cartilage 100 move to the center axis of the body, the epiglottis 810 is folded down, and the vocal folds (not shown) are adducted. To be more specific, when the distance L3 becomes longer than the distance L2, the movement of the epiglottis 810 is normal. On the other hand, when the distance L3 does not become longer than the distance L2, there seems to be a failure in the movement of the epiglottis 810.

Figure 8D:
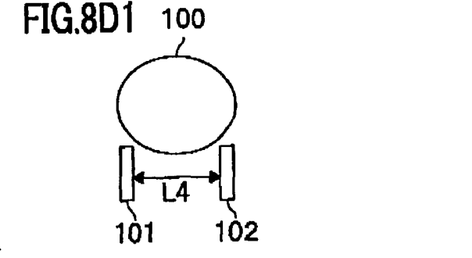
Figures 8D, 8E:
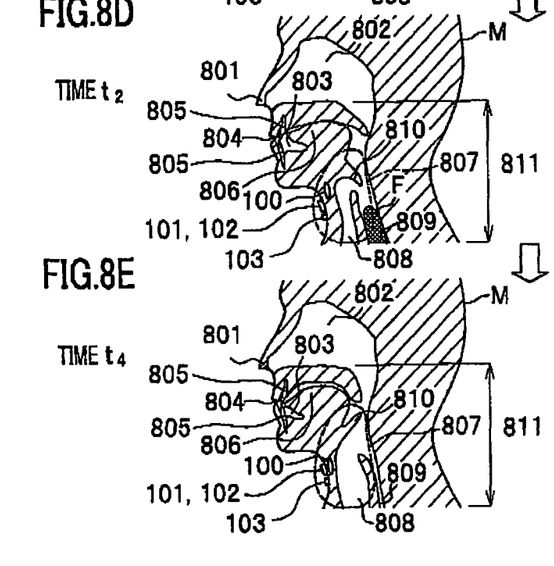
Figure 8E:
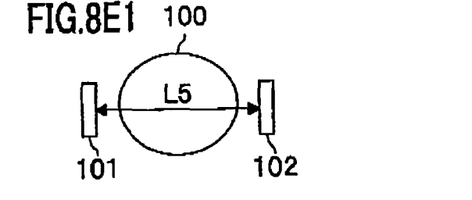

At the time t2, the epiglottis 810 is little relaxed and the distance L4 becomes almost the same as the distance L2 at the time t1. It is thought that the distance waveform of a healthy subject is diphase waveform because the movement described above occurs in the healthy subject. In accordance with the swallowing test apparatus 1000 according to the present invention, it is possible to identify dysphagia correctly based on the shape of the distance waveform and a delay of the peak time of the swallowing sound and the like.

As described above, the swallowing test apparatus 1000 according to the embodiment makes it possible to simplify the test of dysphagia and to display the result of the simplified test. More specifically, the swallowing test apparatus 1000 can realize a test method in which dysphagia is determined easily based on the characteristics of the swallowing movement of the subject M, which is clinically more useful than conventional test methods.

In the swallowing test apparatus 1000, the full-wave rectifier circuit 210 performs full wave rectification on the swallowing sound waveform, and an envelope of the rectified waveform is detected through the LPF circuit 211 so that the characteristics of the swallowing sound is extracted easily.

The button 106 also allows the user of the swallowing test apparatus 1000 to easily detect the swallowing movement start time.

The swallowing test apparatus 1000 displays the distance waveform and the swallowing sound waveform at the same time, and further displays several parameters calculated based on the peak time of the swallowing sound together with the distance waveform and the swallowing sound waveform so that dysphagia associated with aging or brain diseases can be visually and quantitatively determined.

Moreover only the flexible holder 109 and the flexible holder 110 are placed on the subject M, and thus the subject M feels less unpleasant or uncomfortable compared with the conventional methods in which electrodes or the like have to be placed on the subject M.

Embodiments of the present invention are not limited to the embodiment described above. An acceleration sensor may be employed instead of the oscillation coil 101 and the detection coil 102 to detect the lateral displacement of the laryngeal part of the subject M.

The swallowing test apparatus of the present invention can also be used to visualize the achievement of the rehabilitation of dysphagia.

The flexible holder 109 or 110 for holding the oscillation coil 101, the detection coil 102 and the microphone 103 may include an adjuster for adjusting the length of the flexible holder 109 or 110 in accordance with the individual differences of subjects, such as the thickness of the neck.

The reference values may be predetermined by a doctor or the like, or mean value derived from statistical data on a plurality of healthy subjects may be used as the reference values.

The embodiment according to the present invention has been explained as aforementioned. However, the embodiment of the present invention is not limited to those explanations, and those skilled in the art ascertain the essential characteristics of the present invention and can make the various modifications and variations to the present invention to adapt it to various usages and conditions without departing from the spirit and scope of the claims.

What is claimed is:

1. A swallowing test apparatus comprising:
   a laryngeal part displacement detection apparatus configured to detect a distance between two positions located laterally at a laryngeal part of a patient;
   a swallowing sound detection apparatus configured to detect a swallowing sound of the patient during swallowing;
   a processing apparatus configured to generate a waveform representing the distance of the two positions at the laryngeal part generated based on a signal obtained from the laryngeal part displacement detection apparatus, and a waveform representing the swallowing sound generated based on a signal obtained from the swallowing sound detection apparatus;
   a display configured to display the distance waveform and the swallowing sound waveform in response to the processing apparatus generating the distance waveform and the swallowing sound waveform; and
   an operation apparatus which is to be operated by the patient or a person who examines the patient when swallowing, the processing apparatus being configured to:
   detect a peak time of the swallowing sound when the swallowing sound is at maximum based on the signal obtained from the swallowing sound detection apparatus, and
   calculate an amount of characteristics of the swallowing based on at least one of a time interval between a time when the operation apparatus is operated and the peak time of the swallowing sound, a time when the distance between the two positions at the laryngeal part is at minimum before the peak time of the swallowing sound, and a time when the distance between the two positions at the laryngeal part is at minimum after the peak time of the swallowing sound, wherein
   the display is furthered configured to display the calculated amount of characteristics of the swallowing.

2. A swallowing test apparatus according to claim 1, wherein the swallowing sound detection apparatus being formed to include a microphone configured to be positionally disposed at the laryngeal part of the patient,
   the laryngeal part displacement detection apparatus being formed to include a oscillation coil and a detection coil configured to be positionally disposed at the laryngeal part of the patient,
   the processing apparatus is configured to detect the peak time of the swallowing sound based on an envelope of a signal from the microphone, and to calculate at least one of
   the time when the distance between the two positions at the laryngeal part is at the minimum before the peak time of the swallowing sound and
   the time when the distance between the two positions at the laryngeal part is at the minimum after the peak time of the swallowing sound based on an envelope of a signal output from an amplifier circuit which amplifies voltage induced in the detection coil by the oscillation coil.

3. A swallowing test apparatus according to claim 2, further comprising:
   a full-wave rectifier and a low pass filter formed to full-wave rectify and filter the signal from the microphone so as to remove high frequency components, wherein
   the processing apparatus detects the swallowing sound based on the full-wave rectified and filtered signal.

4. A swallowing test apparatus according to claim 2, wherein the oscillation coil and the detection coil are further configured in the laryngeal part displacement detection apparatus so as to be positionally disposed on sides of a thyroid cartilage at the laryngeal part of the patient.

5. A swallowing test apparatus according to claim 2, further comprising:
   at least one flexible holder for holding the microphone, the oscillation coil and the detection coil.

6. A swallowing test apparatus according to claim 1, wherein the processing apparatus is configured to determine whether or not the waveform representing the distance between the two positions at the laryngeal part includes two peaks.

7. A swallowing test apparatus according to claim 1, wherein the processing apparatus is further configured to generate a determination result in response to determining
   whether or not the time interval between the time when the operation apparatus is operated and the peak time of the swallowing sound is within a predetermined range,
   whether or not a time interval between the peak time of the swallowing sound and the time when the distance between the two positions at the laryngeal part is at the minimum before the peak time of the swallowing sound is within a predetermined range, and
   whether or not a time interval between the peak time of the swallowing sound and the time when the distance between the two positions at the laryngeal part is at the minimum after the peak time of the swallowing sound is within a predetermined range; and
   wherein the display is further configured to display the determination result of the processing apparatus.

* * * * *